United States Patent [19] [11] Patent Number: 4,616,134
Pruett et al. [45] Date of Patent: Oct. 7, 1986

[54] HIGH RESOLUTION GEOLOGIC SAMPLE SCANNING APPARATUS AND PROCESS OF SCANNING GEOLOGIC SAMPLES

[75] Inventors: Frank D. Pruett, Walnut Creek; Floyd F. Sabins, Jr., Fullerton, both of Calif.

[73] Assignee: Chevron Research Company, San Francisco, Calif.

[21] Appl. No.: 631,662

[22] Filed: Jul. 17, 1984

[51] Int. Cl.[4] .......................... G01V 5/00; G01F 23/00
[52] U.S. Cl. ................................. 250/255; 250/339; 250/358.1; 356/303
[58] Field of Search .............. 250/253, 255, 338, 339, 250/358.1, 359.1, 372; 356/302, 303, 317, 318, 429

[56] References Cited

U.S. PATENT DOCUMENTS 3,427,861  2/1969  Maley ........................... 250/358.1
4,149,805  4/1979  Chew, III ........................ 250/255
4,247,770  1/1981  Welch ............................ 250/253
4,337,396  6/1982  Lauer et al. ..................... 250/255
4,433,239  2/1984  Thompson ....................... 250/255

OTHER PUBLICATIONS

"Geological Scanner to be Developed", Science/Technology Concentrates (May 14, 1984).
"Mineralogic Information from a New Airborne Thermal Infrared Multispectral Scanner" A. B. Kahle et al., Science, vol. 222 (Oct. 7, 1983).

Primary Examiner—Janice A. Howell
Attorney, Agent, or Firm—S. R. LaPaglia; E. J. Keeling; A. Stephen Zavell

[57] ABSTRACT

An apparatus and process of analyzing samples using reflected and/or emitted radiation is described. The apparatus includes a means for containing the sample and moving the sample and/or a reflector at a uniform rate through a fixed plane. A radiation source irradiates the core sample. The reflected or emitted radiation is directed onto a detector means capable of forming electrical signals which are digitally encoded and recorded on a digital recorder for further interactive analysis and/or processing.

25 Claims, 1 Drawing Figure

U.S. Patent     Oct. 7, 1986     4,616,134
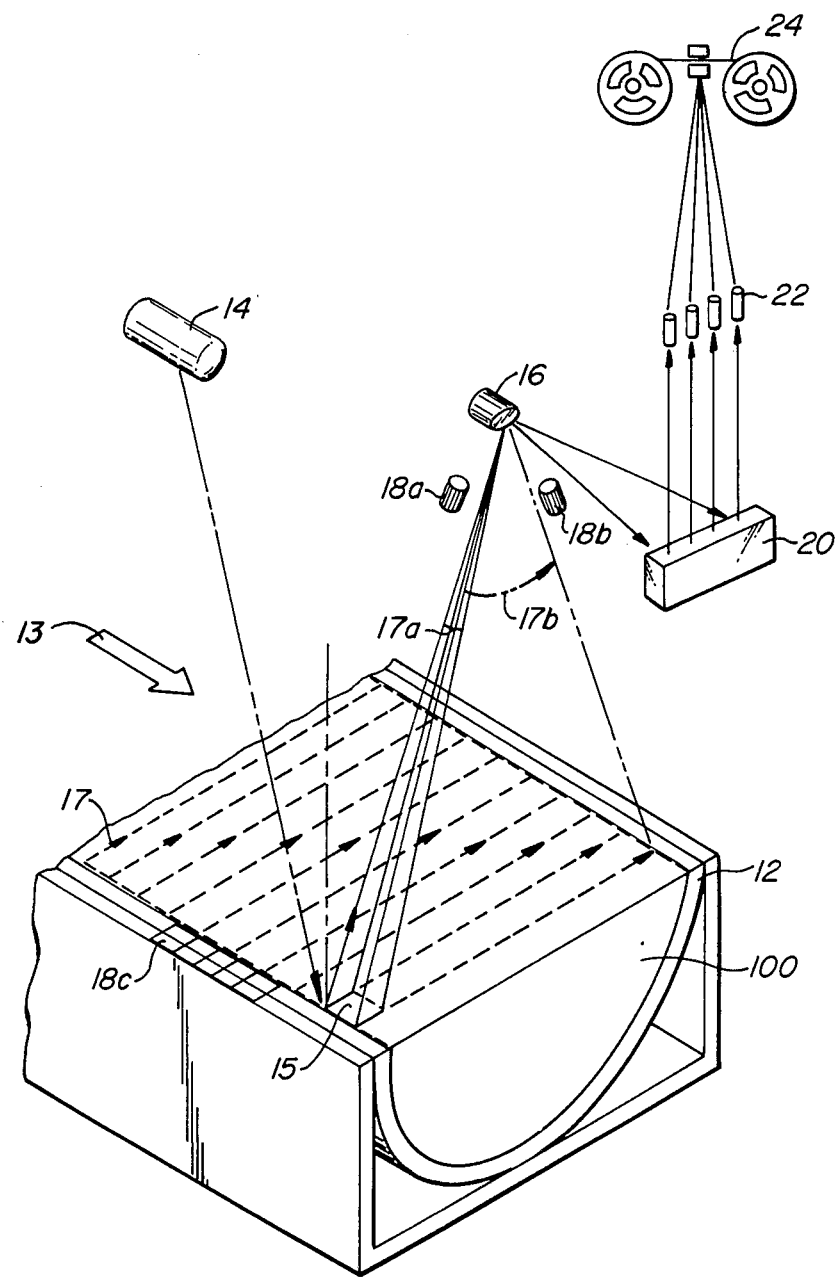
FIG._1.

HIGH RESOLUTION GEOLOGIC SAMPLE SCANNING APPARATUS AND PROCESS OF SCANNING GEOLOGIC SAMPLES

The invention relates to analyzing geologic samples. More specifically, the invention relates to an apparatus capable of obtaining multispectral scanned data of well bore cuttings and/or well bore cores and a process of scanning these geologic samples.

BACKGROUND OF THE INVENTION

As the prospecting industries, such as the oil-gas and mining industries, discover the easily identified deposits (accumulations) of minerals and oil and gas, the search for new reserves and supplies of these materials becomes increasingly difficult and costly. During the exploration for these accumulations and following the discovery of these accumulations, extensive further analysis of well bore cuttings and core samples is required to determine if it is economically feasible to proceed with commercial development.

Petrographic, x-ray and chemical analysis of the well bore, well bore cuttings and core samples are costly and extremely time-consuming. Thus, it would be desirable to have an apparatus and process of analyzing drill cuttings and well bore, well bore cores which can supplement or replace current time-consuming and analytical processes, but yield greater amounts of data more precisely and rapidly from a larger number of samples within a reasonable period of time.

Satellite and airplane scanning/imaging, hereinafter "scanning", of broad geographic areas has been used before in attempts to locate potential sites for further exploration and/or evaluation. However, due to the coarse spatial resolution of these scanning techniques, they are only useful for locating general areas of potential commercial interest. These scanning techniques usually involve the measurement of reflected solar infrared radiation and emitted black-body infrared radiation. Due to atmospheric interference and absorption, measurement of reflected radiation at shorter than about 0.3 $\mu$m wavelengths provides very little, if any, useful information. In addition, satellite and airplane scanning are limited solely to viewing the surface geology of the area.

Thus, it would also be desirable to have an apparatus and process to efficiently scan and image or analyze geological cuttings and/or core samples to determine if further investigation is warranted. In addition, it would be desirable to have a technique which can extend satellite and airplane scanning technology to investigate a wider range of electromagnetic radiation wavelengths to provide additional information in analyzing these samples. Furthermore, it would be desirable to have an apparatus and process which can measure additional properties, such as differential thermal reflectance. This additional measurement is made by the heating of the sample and then measuring the change in thermal infrared radiation (radiant temperature) emitted as the sample cools. Other desirable attributes of an apparatus and process of analysis would be to measure long wavelength reflected IR to determine types of oil in a core sample and the relative saturations of the cuttings or core sample. Additional desirable applications of such an apparatus and process would be to identify and define the location of different clays and cements, provide a means for distinguishing between rocks which are normally difficult to distinguish, such as quartz and opal CT, and delineate porosity variations in the core samples in hopes of providing superior, enhanced oil recovery methods for known discovered deposits/accumulations of minerals and hydrocarbons.

SUMMARY OF THE INVENTION

We have invented an apparatus for and a process of analyzing samples such as cores, well bore cuttings, rock thin sections, mined minerals, and the like quickly and efficiently. The apparatus and process produce the desired analyses previously recited. The apparatus includes a means for containing a sample. The containing means is connected to a means for moving the sample relative to a reflecting means. The reflecting means is located in a plane above the sample to direct the reflected radiation along a predetermined plane. The reflecting means further includes a means for scanning the reflecting means across the sample while maintaining the reflected radiation within the predetermined plane.

A spectrometer is located in the plane of reflected radiation. The spectrometer is capable of receiving reflected radiation from the sample and dividing it into a predetermined number of discrete bands of radiation from the ultraviolet through the infrared. Preferably, the spectrometer divides the reflected radiation into the reflected infrared from about 1 $\mu$m to about 2.5 $\mu$m, the visible and near infrared from about 0.4 to about 1.0 $\mu$m, the thermal infrared from about 8 to about 14 $\mu$m, and the ultraviolet from about 0.2 to about 0.4 $\mu$m. Subdividing the 8 to 14 $\mu$m regions permits the scan image to distinguish between silicate rocks and carbonate rocks due to fundamental Si-O vibrations. The higher the degree of spectral resolution, the more accurate the analysis, especially in the reflected infrared region of from about 1.7 to about 2.4 $\mu$m. However, suitable spectral resolutions for the infrared and near infrared are on the order of about 0.05 $\mu$m or less and from about 0.1 $\mu$m to about 0.2 $\mu$m for the thermal infrared. The apparatus further includes an electromagnetic radiation source(s) directed towards the sample and a calibration source(s) located in the plane of reflected radiation and/or alongside the sample. These create known color densities, colors or thermal radiation peaks for comparison with the sample being evaluated.

The output from the spectrometer is directed towards a detector mean(s). The detector(s) are capable of producing digital data from the analog wavelength bands of radiation. The detectors are selected to be responsive to the desired radiation bands. Finally, the data is recorded on a digital recorder for further interactive processing and to produce sample scan images.

Of course the higher the resolution, the better, but the reflector means-spectrometer is typically located so as to be able to resolve portions of the sample having dimensions of less than about 1 mm by about 1 mm and preferably less than about 0.5 mm by about 0.5 mm and most preferably less than about 0.1 mm by about 0.1 mm. This most preferred surface resolution size (picture elements), although requiring vast amounts data volume, would produce a processed image which is equal to or better than color photography. In addition, the scanner images surpass color photographs for conveying information about the sample because the scanner is more sensitive to reflectance variations than the human eye, it can detect and record wavelengths such as the reflected infrared which cannot be seen by the human eye or recorded on color photographic film, and the digital recording of the image permits its manipulation and enhancement by computer processing to calculate, inter alia, rock type and mineral distribution.

The process of analyzing the sample involves employing the apparatus previously described and irradiating the sample with radiation having a predetermined wavelength distribution. The reflected radiation from the sample is directed by a reflector such as a mirror onto a spectrometer which divides the radiation into selected wavelength bands of radiation and then focuses this radiation onto suitable detectors such as photo-conductors or photovoltaic cells capable of converting the radiation into an electrical signal. Thereafter, the electrical signal from these devices is encoded digitally for further digital processing to produce a correlative image of the sample. Through the appropriate processing, such as mixing recorded radiation wavelength bands and/or biasing certain colors, the sample image can the manipulated to highlight and emphasize framework, composition, and texture of the sample and enable the determination of types of oil and other fluids contained in the sample and the relative fluid saturation of the sample. In addition, the processing can delineate various porosities and distinguish closely-allied rocks, such quartz from opal CT, and help map distribution of clays and cements.

BRIEF DESCRIPTION OF THE DRAWING

The FIGURE illustrates an embodiment of a scanning apparatus of our invention.

DETAILED DESCRIPTION OF THE INVENTION

An apparatus for carrying out the process of our invention is illustrated as apparatus 10 in the FIGURE Although the apparatus 10 can be used to analyze mined minerals, well bore cuttings or well bore core samples, it will be described for the analysis of well bore core samples. The apparatus 10 includes a holder 12 for positioning a core sample 100. Core samples are cylinders extracted from the geological formation during drilling. The core samples are typically cut into two halves to expose the inner portion of the core sample. The holder 12 will have a shape which can contain a half cylinder of the core sample placed therein. A standard U-shaped holder having a width across the mouth of about 15 cm, and a depth of about 10 cm, with a radius of about 10 cm, is suitable. The length of the holder is limited only by the length of core sample to be analyzed. The holder is connected to a core transport system capable of moving the core sample in a fixed plane and direction 13 while maintaining a fixed distance from a reflector means 16. Depending upon the reflector means, a suitable distance from the sample is from about six inches to about 12 feet. Preferably, the reflector means such as a scanning mirror is adjusted to provide an instantaneous field of view 17a of about 0.62 mrad. This is far superior to airplanes or satellites instantaneous fields of view on the order of about 2.5 mrad. In addition, the angular field of view is reduced from about 100 degrees to about 22 degrees. The angular field of view 17b is adjusted to cover the width of the holder 12. A suitable core transport system is a worm-drive geared system connected to the base of core holder 12. Suitable worm-drive gears and transport motors are available from the Daedalus Enterprises, Incorporated.

The apparatus further includes at least one electromagnetic radiation source 14 for irradiating the core sample. The radiation source 14 will contain a source of electromagnetic radiation having the specific wavelength bands of interest. The radiation source can irradiate preferably from the ultraviolet through the far infrared. A suitable broad band radiation source is a quartz-halogen lamp. Alternatively, the radiation source can be any number of individual sources having predetermined radiation wavelengths, such as GaAs lasers, GaP lasers, U.V. helium cadmium lasers, and the like. Optionally, not illustrated, the apparatus includes a means for heating the core sample so that measurements of thermal infrared radiation can be measured. Alternatively, the core sample can be heated in an external oven and then placed in the core holder 12.

A reflector means 16, such as a scanning mirror, scans the core sample as it passes through the scan plane perpendicular to the sample. The reflector further includes a scanner control to control the motion of the reflector. A suitable scanning motion 17 is along the axis of rotation of the reflector, i.e., scan mirror, is parallel to the plane of the core surface being scanned. The resulting scan lines are parallel lines oriented normal to the long axis of the core. Alternatively, the scanning motion of the reflector is controlled such that the axis of rotation of the scan mirror is normal to the plane of the core surface being scanned. The resulting scan lines are parallel circles on the core surface. The only limitation on scanning of the core is that it be done in a uniform manner so that comparisons can be made between the scans of different core samples.

The scanning mirror 16 reflects the radiation from the core sample along a fixed plane onto a spectrometer 20. Optionally, lenses, not shown, can be used to diverge or converge the radiation from the reflector 16. The distance from the sample to the reflector means 16 and the reflector means 16 to the spectrometer 20 is adjusted so that the detector means is capable of resolving areas 15 at least 1 mm by 1 mm of the sample, preferably, resolving areas finer than about 0.5 mm by 0.5 mm and most preferably, resolving area finer about 0.1 mm by about 0.1 mm as it sweeps across the core surface. The absolute levels of reflected energy are calibrated with calibration sources 18a, b, and c. Suitable calibration sources 18a and b for calibrating thermal infrared are uniform high or low temperature sources. As the scanning mirror moves across the sample, it sees the high temperture source at the beginning and the low temperture source at the end or vice versa. Sources 18c are pure color squares such as red, blue, green, and the like or known shade densities of the same color. These sources give the recorded data prespective. These sources are available from Daedalus Enterprises, Incorporated. A suitable spectrometer can also be obtained from Daedalus Enterprises, Incorporated. Due to the short distances involved, the wavelengths around 1.4 $\mu$m, 1.9 $\mu$m, and 2.6 $\mu$m can be used for analysis because atmospheric $CO_2$ and water vapor cause only a 15% reduction of transmittance in the apparatus configuration. These wavelength cannot be used by airborne or satellite systems. This is another advantage of our apparatus.

The spectrometer 20 is configured to divide the reflected radiation into discrete bandwidths and focus the reflected radiation onto the photo-detectors 22. Suitable detectors are photo-conductor cells, photovoltaic cells, or mixtures thereof. Suitable detectors InSb so for reflected radiation from about b 1.55 $\mu$m to about 2.35 $\mu$m, HgCdTe from about 8.5 $\mu$m to about 13 $\mu$m, and Cds, Si, and GaAs for the visible and near infrared. The detectors 22 create an electrical signal based upon their irradiation by that discrete portion of the radiation separated by the spectrometer. The electrical signal from the detectors 22 is amplified if needed and encoded digitally. Thereafter, the digital signal is recorded by digital recorder 24 for image reconstruction and manipulation of the recorded radiation with suitable processing such as with IDIMS, incorporated herein by reference, a product of ESL Incorporated, a subsidiary of TRW, Inc., on a general purpose computer such as a VAX 11/780, a product of Digital Equipment, Inc. The IDIMS routines are used to read the digitally recorded data, enhance contrast and brightness, enhance edges, perform classifications, principal components, and color transformations and make image hard copies.

Although we have described specific embodiments of our invention comprising the apparatus to analyze core samples, the broadest limits of our invention are covered by the process of analyzing core samples. The apparatus can be configured in any fashion using available detectors, drive units, reflectors, and the like. The process covers irradiating a core sample with radiation having a predetermined wavelength distribution as the sample travels along its path. The reflected radiation from the core sample is focused or directed onto a spectrometer capable of dividing the reflected radiation into predetermined wavelength bands and suitable detectors capable of converting the divided radiation into an electrical signal. The electrical signals from the detector are encoded digitally as digital data and recorded for processing so as to produce a correlative image(s) of the core sample. Preferably, the apparatus is adjusted so that during the process of analysis, the resolution of areas of the core samples is finer than 1 square millimeter, and preferably finer than 0.5 mm by 0.5 mm, and most preferably finer than 0.1 mm by 0.1 mm.

Having described the invention with reference to particularly preferred embodiments, it should be understood that modifications which would be obvious to the ordinary skilled artisan are intended to be within the scope of the invention. For example, the sample can be held in a fixed position and the reflector can be moved along the sample. Alternatively, the spectrometer can be located at the position of the reflector to eliminate the requirement for it. Additionally, the apparatus can scan drill pipe, well bores, cement, and any application where high resolution analysis is desired.

What is claimed is:

1. An apparatus for analyzing the reflected radiation from a geologic sample comprising:
   means for holding a sample in a fixed plane;
   means for moving said sample at a uniform rate along said fixed plane connected to said holding means;
   means for irradiating the sample with a source of electromagnetic radiation;
   reflector means located in a plane above the sample and oriented at an angle and distance therefrom such that said reflector means is capable of receiving reflected/emitted radiation from said sample and directing said reflected/emitted radiation along a predetermined plane;
   means for moving said reflector means connected thereto;
   a spectrometer located in the plane of reflected/emitted radiation, said spectrometer capable of dividing said reflected radiation into predetermined energy bandwidths and directing said predetermined energy bandwidths towards detector means, said reflector means and said spectrometer adjusted to have a sample spatial resolution finer than about 1.0 mm by about 1.0 mm.
   detector means responsive to said predetermined energy bandwidths, said detector means capable of converting said predetermined energy bandwidths into electrical signals;
   means for encoding the electrical signals digitally from said detector means; and
   means for recording said digitally encoded signal.

2. The apparatus according to claim 1 wherein the detectors are selected from the group consisting of photo-conductor cells, photovoltaic cells, or mixtures thereof and said refector means is a scanning mirror.

3. The apparatus according to claim 2 wherein said scanning mirror is capable of producing a scanning motion in which the axis of rotation of the scan mirror is parallel with the plane of the sample surface.

4. The apparatus according to claim 3 wherein the means for irradiation is selected from the group consisting of lasers, light-emitting diodes, or mixtures thereof.

5. The apparatus according to claim 4 further including calibration sources along said sample and adjacent to said reflector means.

6. The apparatus according to claim 5 further comprising means for heating cooling the sample.

7. The apparatus according to claim 6 wherein the scan mirror and the spectrometer are positioned so as to obtain a resolution of the sample is finer than about 0.1 mm by about 0.1 mm.

8. The apparatus according to claim 2 wherein the means for rotating the scanning mirror is capable of producing an axis of rotation of the scan mirror which is normal to the plane of the sample surface.

9. The apparatus according to claim 8 wherein the means for irradiation is selected from the group consisting of lasers, light-emitting diodes, or mixtures thereof.

10. The apparatus according to claim 9 further including means for heating the cooling sample.

11. An apparatus for analyzing the reflected radiation from a well bore core sample comprising:
    means for holding a core sample in a fixed plane;
    means for heating said core sample connected to said means for holding;
    means for moving said core sample at a uniform rate along said fixed plane connected to said holding means;
    means for irradiating the core sample with a source of electromagnetic radiation;
    a scanning mirror located in a plane above said core sample for directing the reflected/emitted radiation from said core sample along a predetermined plane, said scanning mirror capable of producing a scanning motion in which the axis of rotation of the scanning mirror is parallel with the plane of the core surface;
    a spectrometer located in said predetermined plane, said spectrometer capable of dividing the reflected/emitted radiation into predetermined energy bandwidths;
    photo-detectors responsive to the predetermined energy bandwidths spaced apart from said spectrometer, said photo-detectors capable of converting the predetermined energy bandwidths into electrical data signals, said scanning mirror, said spectrometer and said photodetectors positioned such that said electrical data signals are capable of being processed to analyze portions of said core sample having dimensions finer than about 0.5 mm by about 0.5 mm;

means for encoding the electrical signals digitally; and means for recording said digitally encoded signal.

12. The apparatus according to claim 11 wherein the means for irradiation is selected from the group consisting of lasers, light-emitting diodes, or mixtures thereof.

13. The apparatus according to claim 12 wherein the photo-detectors are selected from the group consisting of HgCdTe, InSb, Si, GaAs, and CdS.

14. The apparatus according to claim 13 further including calibration sources along said sample and adjacent to said reflector means.

15. A process of analyzing a geological sample comprising:

moving said sample at a uniform rate along a fixed plane;

irradiating said sample with radiation having predetermined wavelength distribution;

scanning said sample with a scanning mirror along an axis of rotation which is selected from the group of scanning directions parallel with the plane of the surface of said sample, normal to the plane of the surface of said sample, and combinations thereof;

focusing the reflected radiation from said sample onto a spectrometer;

dividing the reflected radiation into predetermined wavelength bands with said spectrometer;

directing the predetermined wavelength bands from said spectrometer onto a photo-detector, said photo-detector being capable of converting the radiation into an electrical signal;

encoding digitally the electrical signal from said photo-detector as digital data; and processing the digital data to produce a correlative image of the sample having a resolution finer than about 1.0mm by about 1.0 mm.

16. The process according to claim 15 wherein the wavelength(s) of irradiated radiation varies from the ultraviolet portion to the infrared portion of the electromagnetic radiation spectrum.

17. The process according to claim 16 wherein the processing enhances the internal structure of core sample.

18. The process according to claim 17 which further comprises analyzing mineralogically a portion of the core.

19. The process according to claim 18 wherein the data from said mineralogical analysis is used in the digital data processing to determine a continuous mineralogical composition of the sample.

20. The process according to claim 17 which further comprises heating the sample and measuring the emitted thermal infrared radiation so as to determine relative porosity and map distribution of porosity of the sample.

21. The process according to claim 20 wherein the recorded emitted thermal infrared is used to produce an image of apparent thermal inertia wherein apparent thermal inertia is equal to 1-albedo divided by temperature change wherein albedo is the average reflectance in the visible and near infrared region.

22. The process according to claim 16 wherein the processing superimposes different selected wavelength energy bands to produce a scan image having an enhanced visibility for a predetermined geologic property and/or distinguishes between different geologic compositions.

23. A process of analyzing a geological sample comprising:

irradiating a sample with radiation having predetermined wavelength distribution;

focusing the reflected radiation from the sample onto a spectrometer;

dividing the reflected radiation into predetermined wavelength bands with said spectrometer;

directing the predetermined wavelength bands from said spectrometer onto a photo-detector, said photo-detector being capable of converting the radiation into an electrical signal;

encoding digitially the electrical signal from said photo-detector as digital data;

processing the digital data to produce a correlative image of the sample having a resolution finer than about 1.0 mm by about 1.0 mm; and said processing superimposes different wavelengths energy handwidths to produce a scan image having an enhanced visibility for a predetermined geologic property and/or dlstinguishes between different geologic compositions.

24. The process according to claim 23 further comprises analyzing mineralogically a portion of said sample and wherein the data from said mineralogical analysis is used in the digital data processing to determine a continuous mineralogical composition of the sample.

25. The process according to claim 23 which further comprises heating the sample and measuring the emitted thermal infrared radiation so as to determine relative porosity and map distribution of porosity of the sample.

* * * * *